(12) United States Patent
Small et al.

(10) Patent No.: US 10,694,953 B2
(45) Date of Patent: Jun. 30, 2020

(54) INTEGRATED MEDICAL DEVICE

(71) Applicant: Facebook Technologies, LLC, Menlo Park, CA (US)

(72) Inventors: James Small, Langbank (GB); James Ronald Bonar, Erskine (GB); Zheng Gong, Scotstoun (GB); Gareth John Valentine, York (GB); Erdan Gu, Glasgow (GB); Martin David Dawson, Glasgow (GB)

(73) Assignee: Facebook Technologies, LLC, Menlo Park, CA (US)

( * ) Notice: Subject to any disclaimer, the term of this patent is extended or adjusted under 35 U.S.C. 154(b) by 942 days.

(21) Appl. No.: 13/261,923

(22) PCT Filed: Dec. 19, 2012

(86) PCT No.: PCT/GB2012/053191
§ 371 (c)(1),
(2) Date: Jun. 20, 2014

(87) PCT Pub. No.: WO2013/093463
PCT Pub. Date: Jun. 27, 2013

(65) Prior Publication Data
US 2015/0148643 A1    May 28, 2015

(30) Foreign Application Priority Data

Dec. 20, 2011    (GB) ..................................... 1121874

(51) Int. Cl.
*A61B 5/00* (2006.01)
*A61N 5/06* (2006.01)
(Continued)

(52) U.S. Cl.
CPC ........ *A61B 5/0084* (2013.01); *A61B 5/04001* (2013.01); *A61B 5/4064* (2013.01);
(Continued)

(58) Field of Classification Search
CPC .. A61B 2018/00434; A61B 2562/0612; A61B 2562/0651; A61B 2562/0238; A61B 2562/0233; A61B 5/04001; A61N 5/0622
See application file for complete search history.

(56) References Cited

U.S. PATENT DOCUMENTS

2004/0243021 A1* 12/2004 Murphy ............... A61B 5/4824
600/549
2005/0283148 A1* 12/2005 Janssen .............. A61B 18/1477
606/34
(Continued)

FOREIGN PATENT DOCUMENTS

| WO | 2010083170 A2 | 7/2010 |
| WO | 2011051401 A1 | 5/2011 |
| WO | 2011068696 A2 | 6/2011 |

OTHER PUBLICATIONS

PCT, Written Opinion of the International Searching Authority, EPO.
(Continued)

*Primary Examiner* — Alyssa M Alter
(74) *Attorney, Agent, or Firm* — Fenwick & West LLP (57) ABSTRACT

There is herein described light emitting medical devices and a method of manufacturing said medical devices. More particularly, there is described integrated light emitting medical devices (e.g. neural devices) capable of being used in optogenetics and a method of manufacturing said medical devices.

21 Claims, 5 Drawing Sheets

(51) Int. Cl.
    *A61B 5/04*     (2006.01)
    *H01L 31/16*     (2006.01)
    *H01L 31/18*     (2006.01)
    *H01L 33/00*     (2010.01)
    *H01L 33/32*     (2010.01)
    *A61B 18/00*     (2006.01)
    *A61B 17/00*     (2006.01)

(52) U.S. Cl.
    CPC ............ *A61N 5/0622* (2013.01); *H01L 31/16* (2013.01); *H01L 31/18* (2013.01); *H01L 33/0075* (2013.01); *H01L 33/32* (2013.01); *A61B 2017/00026* (2013.01); *A61B 2018/00434* (2013.01); *A61B 2018/00839* (2013.01); *A61B 2018/00875* (2013.01); *A61N 2005/0612* (2013.01); *A61N 2005/0651* (2013.01); *A61N 2005/0659* (2013.01); *A61N 2005/0662* (2013.01)

(56) References Cited

U.S. PATENT DOCUMENTS

| | | | |
|---|---|---|---|
| 2007/0167683 A1* | 7/2007 | Couvillon, Jr. | A61B 1/00055 600/118 |
| 2008/0073518 A1* | 3/2008 | Itoh | B82Y 20/00 250/306 |
| 2008/0077198 A1 | 3/2008 | Webb | |
| 2008/0077200 A1* | 3/2008 | Bendett | A61N 5/0618 607/89 |
| 2011/0087311 A1 | 4/2011 | Zorzos et al. | |
| 2011/0125077 A1 | 5/2011 | Denison | |
| 2013/0030274 A1* | 1/2013 | Jamieson | A61B 5/6848 600/377 |

OTHER PUBLICATIONS

PCT International Search Report, PCT Application No. PCT/GB2012/053191, dated Jul. 9, 2013, 8 pages.

\* cited by examiner

INTEGRATED MEDICAL DEVICE

CROSS-REFERENCE TO RELATED APPLICATIONS

This application is a National Phase Application of International Application No. PCT/GB2012/053191, filed Dec. 19, 2012, which is incorporated by reference in its entirety.

FIELD OF THE INVENTION

The present invention relates to light emitting medical devices and a method of manufacturing said medical devices. More particularly, the present invention relates to integrated light emitting medical devices (e.g. neural devices) capable of being used in optogenetics and a method of manufacturing said medical devices.

BACKGROUND OF THE INVENTION

Electrical probes for neural stimulation have been in existence for some time. The study of optogenetics requires illumination of selected areas of treated tissue with light of a specific wavelength and the ability to record the responses of neuron activity in the area. Probes have been developed which allow illumination of an area of tissue by the incorporation of an optical fibre waveguide or an integrated waveguide.

Prior uses of optogenetics have been demonstrated using optical fibres illuminated from a remote source. The remote source typically used is either a relatively expensive laser or a macro LED, the latter having a low optical coupling efficiency, such that only a small fraction of the light is delivered to the fibre. The light emitted from optical fibres is neither collimated nor focussed but, as the numerical aperture of the fibres is typically quite low the light output required (power density) to elicit a response is modest. This has some advantages but the construction of these hybrid probes is prohibitively expensive. Additionally, the spacing between the light source and receptors is not controlled. Typically, only one fibre from an external light source is available on each hybrid probe as the shank width is too small to accommodate multiple fibres. This restricts the emission to one wavelength at any given time, making simultaneous stimulation and inhibition difficult. The fibre is typically placed far away from the probe distal end and light is directed in the direction of the distal end where the sensors are placed so that there is illumination across the detector elements. Consequently, this leads to non-uniform illumination at varying sensor positions (absorption and scattering of the incident light) and optical artifacts caused by the incident light shining on the detector. A possible mechanism to improve this is to etch a hole in the Si probe and placement of the fibre inserted in a trench on the probe backside with a 45° angled facet so that the light is directed out of the plane of the probe. However, this is prohibitively expensive and only very skilled labour would be in a position to fabricate such a structure.

In US 2011/0087311 there is a microstructure probe for delivering light of variable colour and/or power, via a set of integrated light guides, from a source (or set of sources) to regions spatially arranged 3-dimensionally, with a length scale of microns to millimeters. In exemplary embodiments of this invention, a microstructure probe comprises many lightguides and is adapted to be inserted into neural or other tissue. The lightguides run in parallel along at least a portion of the axis of the probe. US 2011/0087311 is incorporated herein by reference.

Most optogenetics activate or silence large populations of a given cell type or pathway. It is therefore a preferred feature of the present invention to provide a neural probe which will enable improved resolution of location between emitter to emitter and emitter to sensor and sensor array. This will greatly increase the power of optogenetics to understand neural activity patterns in brain functions.

It is an object of at least one aspect of the present invention to obviate or mitigate at least one or more of the aforementioned problems.

It is a further object of at least one aspect of the present invention to provide an improved neural probe.

It is a further object of at least one aspect of the present invention to provide a method of manufacturing an improved neural probe.

SUMMARY OF THE INVENTION

According to a first aspect of the present invention there is provided an integrated light emitting neural probe, said integrated light emitting neural probe comprising:

a base region within which there are integrated connection points which are capable of connecting to other electrical components;

extending from the base region there is an integrated elongate probe with a distal tip;

one or more light emitters located in the region of the distal tip of the integrated elongate probe; and one or more integrated detectors.

The present invention therefore relates to medical devices such as neural probes made from at least one integrated light emitter and detector. The neural probes comprise a probe structure and a light emitter of an integrated solid state construction. Optionally, the integrated light emitter may be a monolithically integrated light emitter.

It should be noted that the integrated light emitting neural probe of the present invention is not a waveguide.

The integrated light emitting neural probe may be used in a range of optics situations such as optogenetics.

The integrated light emitting neural probes of the present invention may therefore be used for the illumination of selected areas of treated tissue with light of a specific wavelength or band of wavelengths extending from UV to near IR. The neural probes have the ability to record the responses of neuron activity in the probed area.

The neural probe may have the general structure of a needle-like probe and may be formed from a variety of structures such as gallium nitride on a silicon carrier or gallium nitride on a sapphire carrier.

The shape of the neural probe may be of any suitable shape capable of sub-dermal insertion with minimal tissue damage.

Alternatively, the probe structure may also comprise an indium gallium arsenide and/or aluminium gallium arsenide diode structure that may or may not be supported by a carrier such as sapphire or silicon. Other suitable materials are zinc selenide or gallium phosphide.

The shape of the neural probe may, for example, be cut from the emitting material on the carrier such as sapphire using a laser cutting tool.

By selection of the appropriate gallium nitride material the output wavelength can be accurately defined for each application.

The light emitter may also be shaped to allow collimation, focussing or another means to increase the light emission extraction.

A substrate forming the integrated light emitting neural probe may also carry sensing elements integral to the probe formed at predetermined gaps from the light emitter. Multiple emitters and sensor probes may be constructed at predetermined gaps on a single probe. Emitters of differing wavelengths are also possible through monolithic integration or other means.

The integrated elongate probe may have any appropriate length such as about 100 mm.

The light emitter may be located towards or on the distal tip. The emission wavelength may be out with the visible range.

The light emitter may be any suitable light emitter and preferably an LED. There may be one or more LEDs located on the integrated elongate probe.

The neural probe may be designed to integrate single or multi-excitation and single or multi-detection schemes. Furthermore, the neural probe may be designed to reduce detection of artifacts and at the same time to prevent electrical crosstalk and parasitic capacitance effects. This is possible by having an electrically conductive blocking layer which has the dual function of being a ground plane or two layers, one of which is an electrically conductive ground plane. This can be patterned to minimise overlap with the sensing structure with the other layer being an opaque layer which may or may not be insulating. Furthermore, novel lensing or re-direction of the light may be provided to improve directionality of the light to both reduce artifacts and to increase the power density or increase the extraction efficiency to allow for lower drive currents.

The neural probe may also comprise electrodes for sensing which are integrated into the structure. The neural probe may therefore comprise sensing elements.

The sensing elements may be shielded from direct exposure to the emitting element by a blocking layer. The blocking layer may also be electrically conductive and designed to act as a ground plane. A separate ground plane can also be formed and a separate insulating plane used to provide shielding from the LED drive to minimize optically induced cross-talk via effects such as the Becquerel effect. The ground plane may be designed to have an effective area which results in an effective capacitance of <100 pF between the ground and the detector electrode. The ground plane can also be designed to have features such as cross-hatch to reduce the plate area and therefore the effective capacitance between the sensing detector and ground.

The blocking layer may also be designed to have a thickness where the dielectric value minimises the parasitic capacitance.

The sensing elements may also be designed to reduce electrical cross talk and parasitic coupling effects from the electrical drive signal for the light emitting element to the electrical sensing detector.

The sensing elements may be at discrete sites placed at a known distance from the source.

The sensing elements may be ring shaped detectors surrounding the source in order to ensure uniform detection and reduce capacitance by having a smaller area, allowing higher packing density.

The emission wavelengths are typically but not limited to about 300-1500 nm and preferably about 470 nm for optogenetic stimulation.

The emission wavelengths are typically, but not limited to about 300-1500 nm and preferably about 590 nm for optogenetic inhibition.

The probe structures may be encased in silicon nitride/silicon dioxide films or another suitable material for biocompatibility.

Multiple emitters and sensor groups may be present on each probe.

The LED structure may include a lens or other device to collimate or focus the light output.

The LED structure may include an emitter shaped to increase the light extraction efficiency.

The neural probe of the present invention may therefore comprise a blocking layer which is capable of suppressing Becquerel effects in a sensor array. The blocking layer may be composed of, but is not restricted to aluminium. A metallic or other electrical conductive layer can be used in order to shield the sensor array from electrical coupling effects such as capacitive coupling from pulsed switching of the LED. In one embodiment the ground plane may be constructed as a lattice or a grid in order to minimise overlapping area and unwanted capacitance between the LED drive and probe sensing circuits.

An oxide layer or similar insulating layer is used to encapsulate the blocking layer and isolate it from the sensor array. Sensor metal arrays are defined on top of this insulating layer. The sensor metal can be, but is not restricted to iridium, gold, platinum or titanium or a combination of metals. While biocompatible metals should be chosen, it is also possible that the sensor array may be encapsulated with a biocompatible material such as, but not restricted to silicon nitride or polyimide. In this case the sensor recording sites should be exposed using an appropriate lithographic process.

According to a second aspect of the present invention there is provided a method of manufacturing an integrated light emitting neural probe capable of being used in optogenetics, said method comprising:

providing a base region within which there are connection points which are capable of connecting to other electrical components;

providing an integrated elongate probe with a distal tip extending from the base region;

providing a light emitter located in the region of the distal tip of the integrated elongate probe; and providing an integrated detector.

The method may manufacture an integrated light emitting neural probe as defined in the first aspect.

A substrate may be used to form the neural probe which may be GaN and other similar materials such as InGaN, GaP or GaAs on a suitable carrier. The substrate will typically be of a flat planar structure.

The process of forming the neural probe may be as follows. The substrate may initially be cleaned using, for example, a solvent and then deoxidized using, for example, $HCl:H_2O$. A layer of metal may then be deposited onto the substrate using, for example, an evaporation technique. The layer of metal may be formed from, for example, Ni and Au. In a particular embodiment the metal layer may be 7 nm of Ni and 14 nm of Au. A photolithography pattern may then be used to form a p mesa pattern. An etching process may then be performed where reactive ion etching (RIE) photolithography may be used to etch the areas of the metal layer away from the p mesa structure. An inductive coupled plasma (ICP) etching process may then be used to etch the areas of the substrate away from the p mesa layer to form mesa. The photoresist p mesa layer may then be removed using solvents. A deposition of a plasma enhanced chemical vapour deposition (PECVD) layer in the form of an oxide layer such as silicon oxide layers may then occur. The PECVD layer may have a thickness of about 350 nm. The PECVD layer may then be roughened using an etching process such as, for example, an Ar RIE plasma etch. A photolith patterning and wet etch process may then be performed to open n and p contact windows. Finally, there may then be a deposition of interconnect layers in the n and p contact windows and along part of the etched substrate area.

According to a third aspect of the present invention there is provided use of the integrated light emitting neural probe defined in the first and second aspects in optogenetics.

According to a fourth aspect of the present invention there is provided an integrated light emitting medical device capable of being used in optogenetics, said integrated light emitting medical device comprising:

a base region within which there are connection points which are capable of connecting to other electrical components;

extending from the base region there is an integrated elongate probe with a distal tip;

one or more light emitters located in the region of the distal tip of the integrated elongate probe; and one or more integrated detectors.

BRIEF DESCRIPTION OF THE DRAWINGS

Embodiments of the present invention will now be described, by way of example only, with reference to the accompanying drawings in which.

BRIEF DESCRIPTION

Generally speaking, the present invention resides in the provision of medical devices such as neural probes made from an integrated light emitter and detector. There may be one or more light emitters and one or more detectors on the neural probes. The neural probes in contrast to prior art devices comprise a probe structure and emitter in an integrated solid state construction. As will be set out below this provides a number of significant technical advantages.

Figure 1:
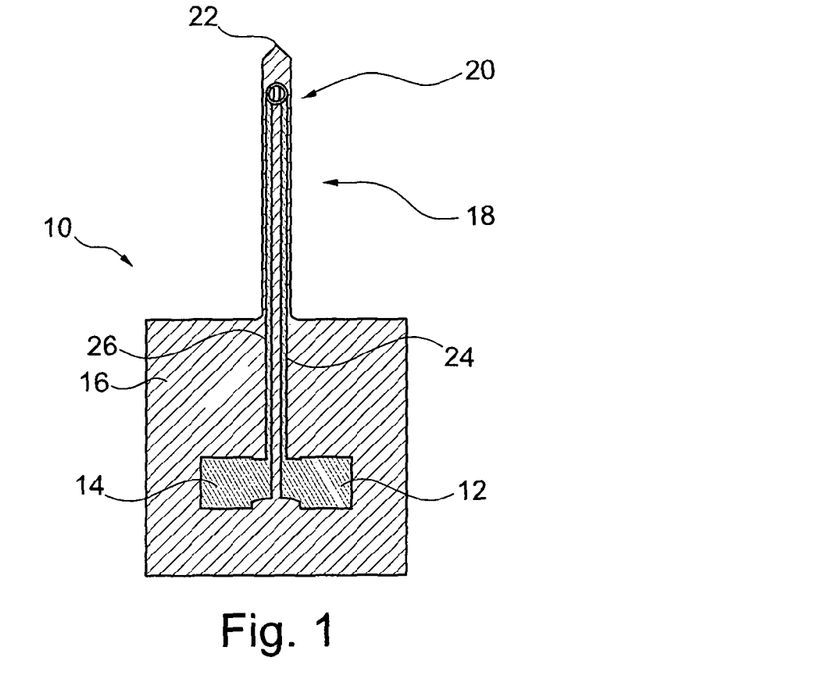
FIGS. 1 and 2 are side views of an integrated light emitting medical device according to an embodiment of the present invention.
Figure 2:
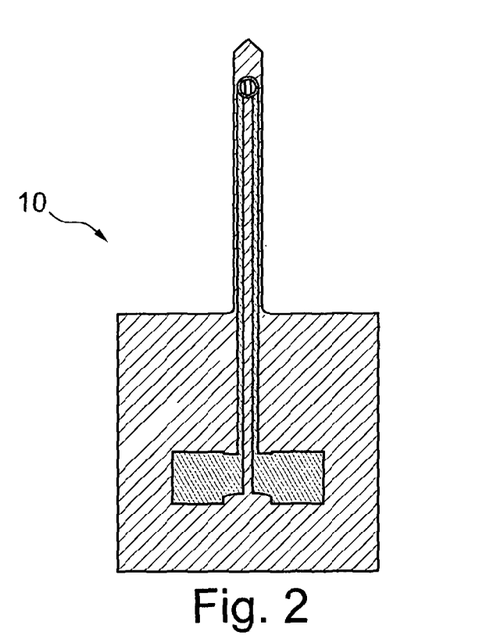

FIGS. 1 and 2 are side views of an integrated light emitting medical device in the form of a neural probe generally designated 10. The neural probe 10 has the general shape of a needle-like probe and may be formed from a variety of structures such as gallium nitride on a silicon carrier or gallium nitride on a sapphire carrier. Alternatively, the probe structure may also be made from indium gallium arsenide and/or aluminium gallium arsenide diode structure supported by a sapphire, silicon or other similar carrier. Other suitable materials are InGaN, GaP InP, AlGaInP, GaAs or similar compound semiconductor material. The shape of the neural probe 10 may, for example, be cut from a sapphire or silicon carrier using a laser cutting tool.

By selection of the appropriate gallium nitride material or colour changing medium the output wavelength can be accurately defined for each application. The emitter structure may also be shaped to allow collimation, focussing or another means to increase the light emission extraction. The substrate may also carry sensing elements integrated into the probe and formed at predetermined gaps from the emitter. Multiple emitters and sensor probes may also be constructed at predetermined gaps on a single probe. Emitters of differing wavelengths are also possible through material selection or other means.

FIGS. 1 and 2 show that the neural probe 10 has a base region 16 within which there are connection points 12, 14 which are capable of connecting to other electrical components. There may be any suitable number of connection points. Extending from the base region 16 there is an elongate probe 18 with a distal tip 22. The elongate probe 18 may have any appropriate length such as about 100 mm. Located towards the end of the distal tip 22 there is an LED 20 which is capable of emitting light. FIGS. 1 and 2 also show that there is electrical circuitry 24, 26 connecting the LED 20 to the connection points 12, 14. It should be noted that the neural probe 10 may be of any suitable shape where the neural probe 10 is capable of sub-dermal insertion with minimal tissue damage.

The neural probe 10 is designed to integrate single or multi-excitation and single or multi-detection schemes. Furthermore, the nature of the neural probe 10 is designed to reduce detection of artifacts and at the same time to prevent electrical crosstalk and parasitic capacitance effects. This is possible by having a blocking layer which has the dual function of being a ground plane or two layers, one of which is a ground plane. This can be patterned to minimise overlap with the sensing structure and the other layer being an opaque layer. Furthermore, novel lensing or re-direction of the light may be provided to improve directionality of the light to both reduce artifacts and to increase the power density for lower drive currents.

The neural probe 10 also comprises electrodes for sensing which are integrated into the structure. The neural probe 10 may therefore comprise sensing elements. As will be described below the sensing elements may be shielded from direct exposure to the emitting element by a blocking layer. The blocking layer can also be designed to act as a ground plane. A separate ground plane can also be formed and acts to shield from an LED drive. The ground plane may be designed to have an effective area which results in a capacitance of <100 pF. The ground plane can also be designed to have features such as cross-hatch to reduce the plate area and therefore reduce the parasitic capacitance.

Figure 3:
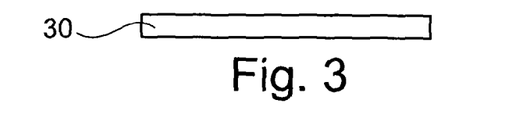
FIGS. 3 to 12 represent the basic process for forming an integrated light emitting medical device according to an embodiment of the present invention.

FIG. 3 is a representation of a substrate 30 made from, for example, GaN. The substrate has a length of about 100 mm and a thickness such as 0.050 mm to 0.350 mm. The substrate is therefore of a flat planar structure which is initially cleaned using, for example, a solvent and then deoxidized using, for example, HCl:H$_2$O.

Figure 4:
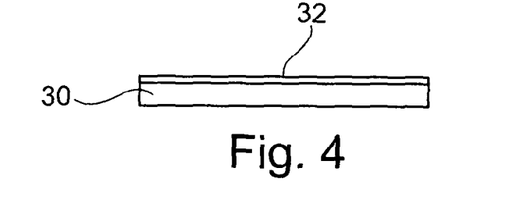

As shown in FIG. 4 a layer of metal 32 is deposited onto the substrate 30 using, for example, an evaporation technique. The layer of metal may be about 2 nm to 20 nm. The layer of metal may be formed from, for example, Ni and Au. In a particular embodiment the metal layer may be 7 nm of Ni and 14 nm of Au.

Figure 5:
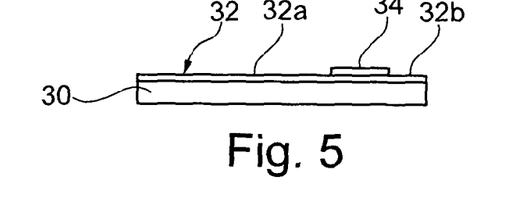

FIG. 5 then shows that a photolithography pattern is used to form a p mesa pattern 34. The p mesa layer 34 has a thickness of about 2 microns.

Figure 6:
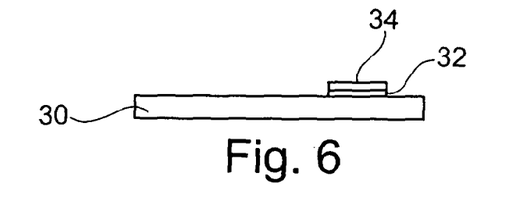

FIG. 6 is a representation of an etching process where reactive ion etching (RIE) photolithography is used to etch the areas of the metal layer 32a, 32b away from the p mesa structure 34.

Figure 7:
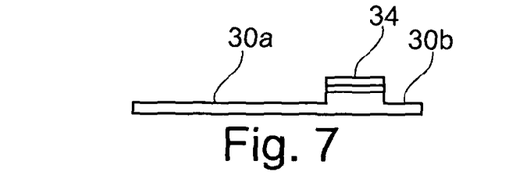

In FIG. 7 an inductive coupled plasma (ICP) etching process then occurs which etches the areas 30a, 30b of the substrate 30 away from the p mesa layer 34 to form mesa.

Figure 8:
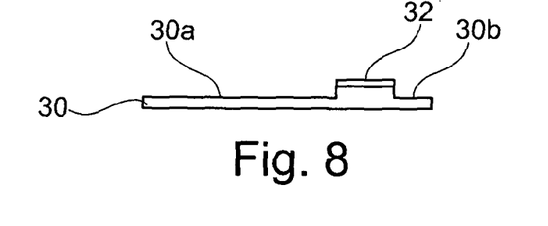

FIG. 8 then represents the step where the photoresist p mesa layer 34 is removed using a solvent.

Figure 9:
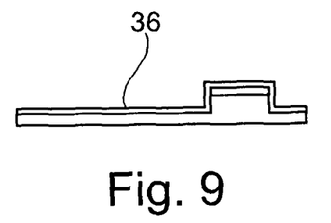

In FIG. 9 there is then a deposition of a plasma enhanced chemical vapour deposition (PECVD) layer 36 in the form of an oxide layer such as silicon oxide layers. The PECVD layer 36 has a thickness of about 350 nm.

Figure 10:
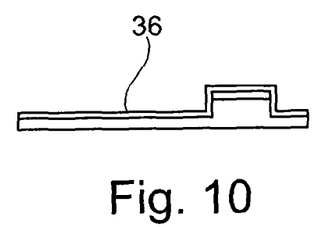

In the next step as shown in FIG. 10 the PECVD layer 36 is then roughened using an etching process such as, for example, an Ar RIE plasma etch.

Figure 11:
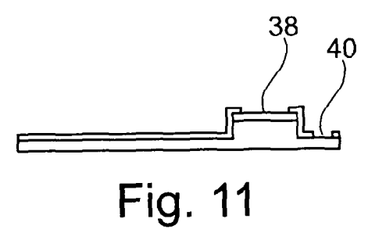

As shown in FIG. 11 there is then a photolith pattern and wet etch process to open n and p contact windows 38, 40.

Figure 12:
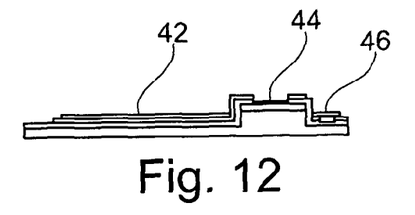

Finally, FIG. 12 shows that there is the deposition of interconnect layers 42, 44, 46 in the n and p contact windows 38, 40 and along part of the etched substrate area.

Figure 13:
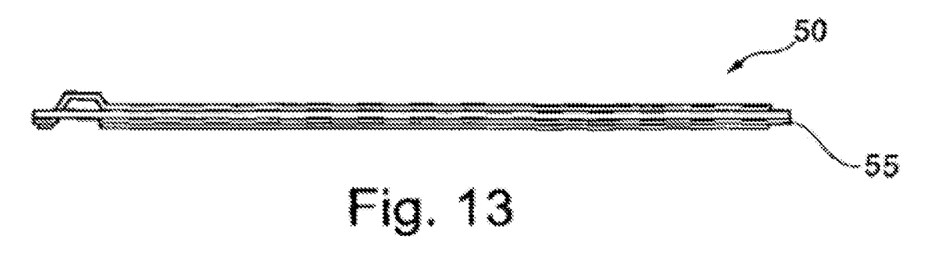
FIG. 13 is a side sectional view of an individual probe and sensor pair according to a further embodiment of the present invention.
Figure 14:
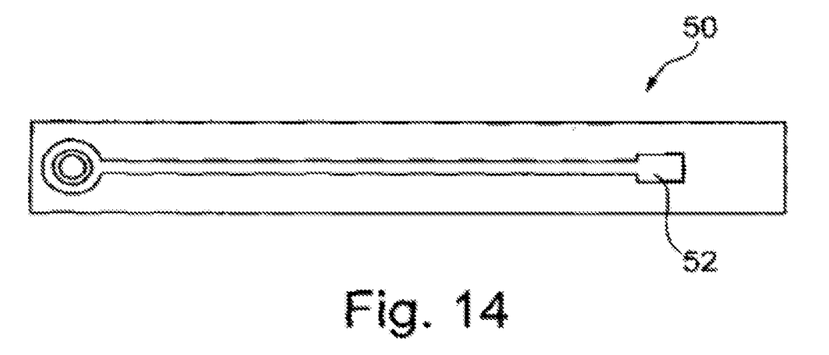
FIG. 14 is an upper face view of the individual probe and sensor pair shown in FIG. 13.
Figure 15:
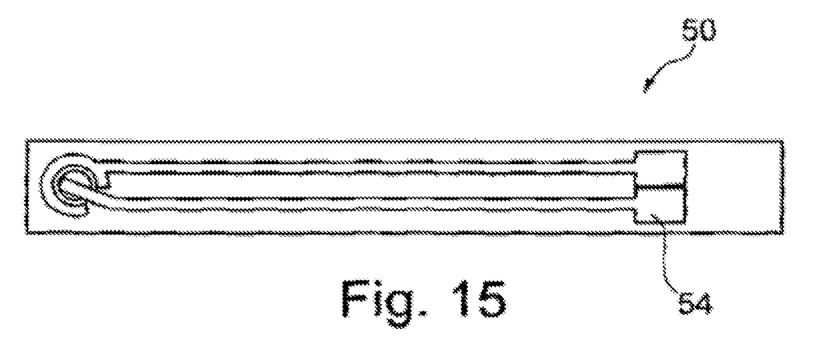
FIG. 15 is a lower face view of the individual probe and sensor pair shown in FIGS. 13 and 14.

FIG. 13 is a side sectional view of an individual probe and sensor pair 50 of the present invention. FIG. 14 is a lower face view of the detector 52 and FIG. 15 is an upper face view of the emitter 54. The individual probe and sensor pair 50 as shown in FIG. 13 has a blocking layer 55 which suppresses Becquerel effects in the sensor array. The blocking layer 55 is shown on the sapphire face. This will have an opening to allow light from the emitter to illuminate the required area while still shielding the sensor metal from direct light exposure. The blocking layer may be composed of, but is not restricted to aluminium. A metallic layer can be used in order to shield the sensor array from parasitic capacitance effects from pulsed switching of the LED. In one embodiment the ground plane may be constructed as a lattice or a grid in order to minimize overlapping area and unwanted capacitance. In this case there should be a supplementing optical blocking layer. An opaque polymer such as but not limited to modified polyimide may be used to supplement or replace the blocking layer in some embodiments. In this case care must be taken in the layout to avoid overlapping feed and sensor tracks to minimise stray capacitance.

An oxide layer or similar electrically insulating layer can be used to encapsulate the blocking layer and isolate it from the sensor array. Sensor metal arrays are defined on top of the insulating layer. The sensor metal can be, but is not restricted to iridium, gold, platinum or titanium or a combination of metals. While biocompatible metals should be chosen, it is also possible that the sensor array may be encapsulated with a biocompatible material such as, but not restricted to silicon nitride or polyimide. In this case the sensor recording sites should be exposed using an appropriate lithographic process.

In one embodiment the recording sensors are formed as a ring structure surrounding the emission source but shielded from the source by the blocking layer. In this configuration the sensor surface is arranged in order to have practically uniform illumination over the entire surface for more accurate results. The area of the sensor element and the underlying insulation material should be selected with appropriate values to match the input impedance requirements of the recording device.

Figure 16:
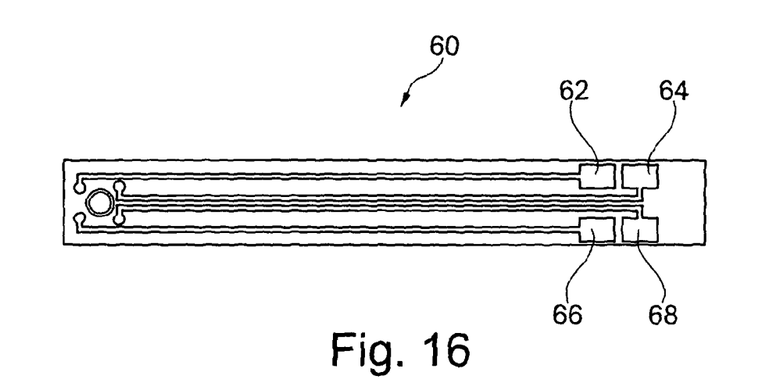
FIG. 16 is a view of a further integrated light emitting medical device according to the present invention.

FIG. 16 is a view of a further integrated light emitting medical device 60 of the present invention where there is a ring configuration and four sensor sites 62, 64, 66, 68.

Whilst specific embodiments of the present invention have been described above, it will be appreciated that departures from the described embodiments may still fall within the scope of the present invention. For example, any suitable type of material may be used to form the integrated light emitting medical devices and any suitable manufacturing process may be used.

In all embodiments, multiple emitter sites and multiple sensor sites may be incorporated in one probe.

The invention claimed is:

1. An integrated light emitting neural probe, comprising:
   a base region including integrated connection points;
   an integrated elongate probe extending from the base region, an end of the integrated elongate probe opposite the base region including a distal tip;
   a light emitting diode (LED) configured to generate light, the LED located at the distal tip of the integrated elongate probe and at a first side of the integrated elongate probe, the LED being coupled to the integrated connection points via electrical circuitry extending through the integrated elongate probe; and
   an integrated detector configured to detect electrical signals indicating responses of neurons illuminated by the LED, the integrated detector located at a second side of the integrated elongate probe opposite the first side.

2. The integrated light emitting neural probe according to claim 1, wherein the integrated detector is located at the distal tip.

3. The integrated light emitting neural probe according to claim 1, wherein the integrated elongate probe with the distal tip has a needle-like structure.

4. The integrated light emitting neural probe according to claim 1, wherein the integrated light emitting neural probe is formed from one of:
   gallium nitride on a silicon carrier or gallium nitride on a sapphire carrier; or
   indium gallium arsenide or aluminium gallium arsenide on a sapphire, silicon, insulating dielectric or compound semiconductor carrier.

5. The integrated light emitting neural probe according to claim 1, wherein the LED includes a shape that increases light emission extraction by the LED.

6. The integrated light emitting neural probe according to claim 1, further comprising a substrate that forms the integrated elongate probe, the substrate including multiple integrated detectors formed at predetermined gaps from the LED.

7. The integrated light emitting neural probe according to claim 1, further comprising a second LED of a differing wavelength to the LED in the integrated elongate probe.

8. The integrated light emitting neural probe according to claim 1, further including a plurality of LEDs including the LED, the plurality of LEDs located on the integrated elongate probe.

9. The integrated light emitting neural probe according to claim 1, further comprising a ground plane in the integrated elongate probe, the ground plane being between the LED and the integrated detector.

10. The integrated light emitting neural probe according to claim 1, further comprising an optical blocking layer in the integrated elongate probe, the optical blocking layer being between the LED and the integrated detector.

11. The integrated light emitting neural probe according to claim 10, further comprising a ground plane to shield detector signals of the integrated detector from an LED drive signal of the LED, the ground plane being between the LED and the integrated detector.

12. The integrated light emitting neural probe according to claim 1, further including a plurality of integrated detectors forming a ring structure.

13. The integrated light emitting neural probe according to claim 1, wherein the LED includes a lens to collimate the light.

14. The integrated light emitting neural probe according to claim 1, further comprising an array of detectors including the integrated detector and an optical blocking layer that suppresses induced cross-talk effects in the array of detectors.

15. The integrated light emitting neural probe according to claim 1, wherein the integrated elongate probe extending from the base region includes a semiconductor material that forms a portion of the LED.

16. The integrated light emitting neural probe according to claim 15, wherein the semiconductor material forms a mesa of the LED that collimates light emitted from the LED.

17. A method of manufacturing an integrated light emitting neural probe, comprising:
    providing a base region from a substrate, the base region including connection points;
    providing an integrated elongate probe extending from the base region, an end of the integrated elongate probe opposite the base region including a distal tip; and
    providing a light emitting diode (LED) configured to generate light, the LED located at the distal tip of the integrated elongate probe and at a first side of the integrated elongate probe, the LED being coupled to the connection points via electrical circuitry extending through the integrated elongate probe; and
    providing an integrated detector configured to detect electrical signals indicating responses of neurons illuminated by the LED, the integrated detector located at a second side of the integrated elongate probe opposite the first side.

18. The method of manufacturing an integrated light emitting neural probe according to claim 17, further comprising:
    cleaning the substrate using a solvent and deoxidizing the substrate using HCl; and
    depositing a layer of metal onto the substrate using an evaporation technique.

19. The method of manufacturing an integrated light emitting neural probe according to claim 18, further comprising:
    depositing a photoresist defining a p mesa structure on the layer of metal; and
    etching areas of the layer of metal away from the p mesa structure using reactive ion etching (RIE) photolithography.

20. The method of manufacturing an integrated light emitting neural probe according to claim 19, further comprising:
    etching areas of the substrate away from the p mesa structure to form a mesa;
    removing the photoresist from the p mesa structure; and
    depositing an oxide layer using a plasma enhanced chemical vapor deposition (PECVD).

21. The method of manufacturing an integrated light emitting neural probe according to claim 17, wherein the integrated elongate probe extending from the base region includes a semiconductor material and providing the LED located at the distal tip of the integrated elongate probe includes fabricating a portion of the LED using the semiconductor material.

* * * * *